(12) United States Patent
Smith et al.

(10) Patent No.: US 7,875,342 B2
(45) Date of Patent: Jan. 25, 2011

(54) POROUS CERAMIC COMPOSITE BONE GRAFTS

(75) Inventors: Timothy J. N. Smith, Kingston (CA); Hendry Jason, Kingston (CA); M. Pugh Sydney, Glenburnie (CA); Smith Reginald, Kingston (CA)

(73) Assignee: Warsaw Orthopedic, Inc.

( * ) Notice: Subject to any disclaimer, the term of this patent is extended or adjusted under 35 U.S.C. 154(b) by 399 days.

(21) Appl. No.: 10/490,492

(22) PCT Filed: Sep. 24, 2002

(86) PCT No.: PCT/CA02/01450

§ 371 (c)(1), (2), (4) Date: Dec. 3, 2004

(87) PCT Pub. No.: WO03/026714

PCT Pub. Date: Apr. 3, 2003

(65) Prior Publication Data

US 2006/0198939 A1     Sep. 7, 2006

(51) Int. Cl.
  *B32B 3/26*  (2006.01)
  *A61F 2/28*  (2006.01)

(52) U.S. Cl. .............. 428/312.2; 428/315.5; 428/315.7; 428/316.6; 428/318.4; 623/23.56; 623/23.58; 623/23.59

(58) Field of Classification Search .............. 428/319.3, 428/319.7, 316.6, 317.9, 312.2, 315.5, 315.7; 623/23.56–23.59
See application file for complete search history.

(56) References Cited

U.S. PATENT DOCUMENTS

| | | | |
|---|---|---|---|
| 3,899,556 A | 8/1975 | Heide et al. | |
| 3,907,579 A | 9/1975 | Ravault | |
| 3,929,971 A | 12/1975 | Roy | |
| 3,946,039 A | 3/1976 | Walz | |
| 3,947,363 A | 3/1976 | Pryor et al. | |
| 3,962,081 A | 6/1976 | Yarwood et al. | |
| 4,004,933 A | 1/1977 | Ravault | |
| 4,164,794 A * | 8/1979 | Spector et al. ............. | 623/23.6 |
| 4,371,484 A | 2/1983 | Inukai et al. | |
| 4,568,595 A | 2/1986 | Morris | |
| 4,610,692 A * | 9/1986 | Eitenmuller et al. ........ | 424/422 |
| 4,629,464 A | 12/1986 | Takata et al. | |
| 4,654,314 A | 3/1987 | Takagi et al. | |
| 4,737,411 A | 4/1988 | Graves, Jr. et al. | |
| 5,282,861 A | 2/1994 | Kaplan | |
| 5,338,772 A | 8/1994 | Dingeldein et al. | |
| 5,456,833 A | 10/1995 | Butcher et al. | |
| 5,458,653 A * | 10/1995 | Davidson .................. | 623/23.36 |
| 5,766,618 A | 6/1998 | Devin et al. | |
| 5,863,984 A | 1/1999 | Doillon et al. | |
| 5,876,446 A * | 3/1999 | Agrawal et al. .......... | 623/23.61 |
| 6,136,029 A | 10/2000 | Johnson et al. | |
| 6,240,926 B1 | 6/2001 | Chin Gan et al. | |
| 6,296,667 B1 * | 10/2001 | Johnson et al. .......... | 623/23.61 |
| 6,323,146 B1 * | 11/2001 | Pugh et al. ...................... | 501/1 |
| 6,518,328 B2 * | 2/2003 | Kumar ........................ | 523/113 |
| 6,527,810 B2 | 3/2003 | Johnson et al. | |
| 6,596,442 B1 | 7/2003 | Wong et al. | |
| 6,626,950 B2 * | 9/2003 | Brown et al. .............. | 623/23.72 |
| 7,122,057 B2 * | 10/2006 | Beam et al. ............... | 623/23.51 |
| 2002/0143403 A1 * | 10/2002 | Vaidyanathan et al. ... | 623/23.51 |
| 2003/0114936 A1 * | 6/2003 | Sherwood et al. ........ | 623/23.58 |

FOREIGN PATENT DOCUMENTS

| | | |
|---|---|---|
| JP | 63181756 A | 7/1988 |
| JP | 2001206787 A | 8/2009 |
| WO | 9532008 A1 | 11/1995 |
| WO | 9746178 A | 12/1997 |
| WO | 9916478 A1 | 4/1999 |
| WO | 9916479 A | 4/1999 |
| WO | 9919003 A1 | 4/1999 |
| WO | 9938542 A | 8/1999 |
| WO | 0071083 A | 11/2000 |
| WO | 0112106 A | 2/2001 |
| WO | 02083194 A | 10/2002 |

\* cited by examiner

*Primary Examiner*—Hai Vo

(57) ABSTRACT

The invention relates to porous ceramic composites incorporating biodegradable polymers for use as a bone substitute in the fields of orthopedics and dentistry or as a scaffold for tissue engineering applications. The porous ceramic composite implant for connective tissue replacement comprises a porous ceramic matrix having a biodegradable polymer provided on internal and external surfaces of the ceramic matrix. The biodegradable polymer allows for the passage and/or delivery of a variety of agents throughout the porous ceramic matrix and improves mechanical properties of the implant in vivo.

21 Claims, No Drawings

POROUS CERAMIC COMPOSITE BONE GRAFTS

FIELD OF THE INVENTION

This invention relates to porous ceramic composites incorporating biodegradable polymers for use as a bone substitute in the fields of orthopedics and dentistry or as a scaffold for tissue engineering applications. The invention further relates to methods for producing such composites alone or in combination with pharmaceutical agents.

BACKGROUND OF THE INVENTION

Currently, the most common practice for replacing damaged or diseased bone is to use autograft (bone removed from the patient). However, high incidences of donor site morbidity, the necessity of a painful second 'harvesting' surgical procedure, and the absence of large quantities of bone available for grafting compromises patient outcomes. Concerns with allografts (bone taken from a cadaver) and xenografts (bone obtained from animals) include: (1) transmission of disease, (2) difficulty of procurement and processing, (3) uncertain immune response, and (4) premature resorption.

As a consequence of the limitations associated with 'natural' grafts, there is significant advantage for the development of synthetic bone grafts that have the potential to offer important advantages, including: elimination of the risk of disease transmission; reduced occurrence of an adverse immunological response; absence of painful 'harvesting' procedure; relatively low costs; unlimited supply; and the ability to incorporate pharmaceutical agents that accelerate the bone healing process.

As the main inorganic component of bone consists of a highly substituted calcium phosphate (CaP) apatite, researchers concerned with developing synthetic bone substitutes have concentrated on the various forms of CaP. These include hydroxyapatite, carbonated apatite, fluroapatite, $\alpha$ and $\beta$ tricalcium phosphate, tetracalcium phosphate, octacalcium phosphate, and combinations thereof. In general, these materials have proven to be both biocompatible and osteoconductive and are well tolerated by host tissues. However, to be an effective bone substitute, these materials must possess the appropriate physical structure and mechanical properties. Of particular concern, structurally, is the level of porosity, pore size, and size of the interconnections between each pore.

Currently commercially available synthetic bone grafts possess low levels of porosity, inappropriate pore size and pore size distribution, and inadequate pore connectivity to permit vascularization of the implant and, thus, do not adequately support tissue in-growth. Another disadvantage of commercially available bone grafts is their poor mechanical properties, which limits the use of these implants to non-load bearing applications. Furthermore, the techniques used to manufacture these implants do not permit the production of porous bodies with gradient porosity or those with a solid cortical shell; necessary properties for applications involving segmental defects.

Mechanical fixation of orthopedic implants can lead to the unintentional release of particulate debris that can migrate into surrounding tissues or articular joints. The presence of this debris can compromise the vitality of surrounding tissues or damage articular surfaces, leading to bone resorption, osteolysis and the failure of such implants over time. As such, another major disadvantages of commercially available synthetic bone grafts is the risk of particulate debris generation and migration arising from the use of standard orthopedic fixation techniques.

There are several patents describing methods of producing porous bodies for use as bone replacements; see for example, U.S. Pat. Nos. 3,899,556, 3,929,971, 4,654,314, 4,629,464, 4,737,411, 4,371,484, 5,282,861, 5,766,618, 5,863,984, WO 95/32008 and WO99119003. A common technique for producing porous ceramic bodies involves the use of pore forming agents as described in U.S. Pat. Nos. 4,629,464, 4,654, 314, 3,899,556 and WO 95/32008. Pore forming agents, however, typically result in a 'closed cell' structure characterized by inadequate pore interconnectivity. It is well known that tissue in-growth into porous materials is a function of both pore size and pore connectivity. Many researchers have attempted to overcome this lack of pore connectivity by increasing the fraction of pore forming agents used and, whilst this does slightly improve pore connectivity, the accompanying loss of mechanical strength makes the resulting structure impractical for clinical use.

U.S. Pat. No. 4,737,411 discloses a method for producing porous ceramics. In this method, a ceramic composite having an open porous network and a controlled pore size is produced by coating ceramic particles, of known size, with a glass coating. These coated ceramic particles were subsequently pressed into the desired shape and sintered such that the glass coating fused the ceramic particles together. Through the close control of the particle size and thickness of the glass coating, the size of the pores formed between the fused particles could be controlled. This technique of forming porous ceramics for bone replacement is somewhat limited, as the maximum pore size obtainable is approximately 150 µm, whilst previous research has shown that pore sizes up to 500 µm are required for optimum tissue in-growth.

U.S. Pat. No. 3,299,971 discloses a method of producing a porous synthetic material for use in hard tissue replacement. In this method, a porous carbonate skeletal material of marine life (coral) is converted into a porous hydroxyapatite material through a hydrothermal chemical exchange with a phosphate. The final microstructure of the converted hydroxyapatite material is essentially the same as that of the coral from which it was formed. Consequently, pore size is dependent on the type of coral used. While these porous structures possess the appropriate pore size and pore connectivity for hard tissue in-growth, the structure is limited to that of the selected coral and so the production of implants with a solid shell surrounding the porous network (typical of cortical or long bone, for example) is unobtainable. In addition, the bone grafts manufactured using this technique are characterized by poor mechanical properties and are difficult to handle and shape and cannot be secured using standard fixation techniques.

Reticulated foams made from an organic material, such as polyurethane, are characterized by pore interconnectivity, high porosity, and are available in a variety of pore sizes. As such, these reticulated structures have been used to manufacture porous bodies of metal or ceramic composition. While typically used in molten metal filtration applications, both ceramic and metal foams manufactured from the coating of reticulated polyurethane networks have found increasing use in orthopaedic and dentistry applications. For example, U.S. Pat. No. 5,282,861 discloses a reticulated carbon foam (converted from polyurethane using a thermal treatment) that was used to manufacture an open cell tantalum foam for use as an implant in both hard and soft tissue. Tantalum was applied to the surface of the carbon foam as a thin film using a chemical vapour deposition (CVD) technique. As such, the Tantalum-coated foam replicated closely the morphology of the reticulated carbon foam substrate. While Tantalum is biocompatible (i.e. inert), it is non-degradable and non-resorbable and, as such, will be implanted permanently. This is also the case with total hip and knee replacements and, while the titanium and cobalt alloys used to fabricate these implants are also considered to be 'biocompatible', long-term implantation of these devices often results in adverse systemic effects such as metal ion sensitization. As a consequence of these problems, it is becoming increasingly desirable to use, where possible, an implant that will eventually be resorbed and replaced with natural, healthy bony tissue.

U.S. Pat. No. 3,946,039 discloses a method to produce porous ceramic or metal structures using reticulated polyurethane foam. In this method a reticulated polyurethane foam is invested with an inorganic composition that is not compromised by the processing conditions required for forming the reticulated ceramic or metal structure. The polyurethane foam structure is removed using a chemical or thermal process, and the voids remaining in the investment are filled with a fluid composition (metal or ceramic) to form a reticulated casting. The final step of this process involves dissolving the investment so as to leave the reticulated ceramic or metal foam structure casting. The disadvantages of this technique are similar to that of the coral conversion method in that the structure of the final part is limited to the structure of the starting foam. Furthermore, the incorporation of a solid outer shell or density gradients is difficult or unobtainable.

Perhaps the most common technique for producing porous bodies from reticulated polyurethane foam is a replication technique, as disclosed in U.S. Pat. Nos. 4,371,484, 6,136,029, 3,947,363, 4,568,595, 3,962,081, 4,004,933, 3,907,579, 5,456,833 and WO 95/32008. In general, this technique involves impregnating a reticulated polyurethane foam structure with a metal or ceramic slurry to deposit a thin film of coating material onto the surface of the foam substrate. Excess slurry is commonly removed from the pores by passing the foam through a set of rollers, centrifuging, or blasting with a jet of air. After the excess slurry has been removed, the reticulated structure is dried and the organic foam substrate removed by pyrolysis. This typically involves heating to temperatures between 200° C. and 500° C. After the pyrolysis of the foam substrate, the temperature is increased for the subsequent sintering of the metallic or ceramic particles.

U.S. Pat. Nos. 5,456,833 and 4,568,595 describe two different methods for forming a solid shell of material around a coated reticulated structure. The former describes the use of a pressed annular ring around a reticulated cylinder while the latter indicates the use of a secondary process where a high viscosity slurry is applied to the outside of the reticulated structure to generate a solid coating following thermal processing in order to improve the strength of the reticulated structure.

U.S. Pat. No. 6,136,029 discloses a method to produce a porous structure suitable for bone substitution comprising a continuous, strong, framework structure of alumina or zirconia using the standard replication technique. In an attempt to provide osteoconductive and/or osteoinductive properties to the porous implant, a second material of osteoconductive/osteoinductive composition was included. The second material could be present in several forms, including (1) a coating on the surface of the framework structure, (2) in the form of a composite, intimately mixed with the framework material, or (3) as a porous mass within the interstices of the framework structure. The second phase materials outlined as being suitable for this invention included osteoconductive materials such as collagen and the various forms of calcium phosphate (hydroxyapatite, tricalcium phosphate, etc.) and osteoinductive materials such as bone morphogenetic proteins (BMP's), demineralized bone matrix, and transforming growth factors (TGF-$\beta$). The variations to the foam replication process as outlined in this patent are important in bone substitution applications as they provide a means to produce a composite implant capable of delivering pharmaceutical agents that may enhance the rate of healing. However, the use of an inert framework structure as a means of providing the implant with improved mechanical properties severely limits the use of this device for hard tissue replacement. As previously mentioned, it is desirable that the implanted material be completely replaced with natural bony tissue.

As the repair or replacement of bony voids or defects is site specific, pharmaceutical agents, such as bone growth factors, must be locally delivered via an appropriate carrier. Biodegradable polymers have been used as drug delivery vehicles as they can be implanted directly at the site of repair and their rate of degradation and, hence, rate of drug delivery can be controlled. However, such biodegradable polymers do not possess the mechanical properties suitable for hard tissue replacement. As such, there has been an increased interest in polymeric/ceramic composites, as disclosed for example U.S. Pat. No. 5,766,618 and WO 99/19003.

U.S. Pat. No. 5,766,618 describes a method of forming a polymer/ceramic composite in which a biocompatible and biodegradable polymer (PLGA) was combined with a calcium phosphate ceramic (hydroxyapatite) in an attempt to improve the mechanical properties of the polymer matrix. While the incorporation of a ceramic phase provided an initial improvement in elastic modulus, immersion of the implant in a simulated physiological environment resulted in a rapid decrease in modulus from 1459 MPa to less than 10 MPa in under six weeks. Clearly, such rapid degradation of mechanical properties limits the use of this device for hard tissue replacement applications.

WO 99/19003 describes an injectable polymer/ceramic gel that is fluid under non-physiological conditions and non fluid under physiological conditions. Composed of natural or synthetic, resorbable or non-resorbable polymers mixed with a ceramic phase, the gel is limited to filling very small bony defects and does not possess the mechanical properties or porous structure for the treatment of large segmental defects.

It is apparent from the aforementioned prior art that a variety of methods have been developed to manufacture porous implants suitable for bone repair and/or replacement. However, current methods and implants possess several shortcomings that make the resultant function of the implant less than satisfactory for prolonged implantation. It would therefore be advantageous to develop a porous implant and method of making such that obviates the shortcomings of the prior art.

The Applicant's U.S. Pat. No. 6,323,146 discloses a synthetic biomaterial compound (Skelite™) composed of silicon-stabilized calcium phosphate. Extensive testing demonstrated that this compound is ideally suited for use as a bone substitute material as it is: (1) 100% synthetic, (2) biocompatible, (3) able to participate in the body's natural bone remodeling process, and (4) relatively inexpensive to produce. U.S. Pat. No. 6,323,146 also describes a method of forming a porous body of the Skelite™ compound by replicating a reticulated organic foam substrate. It is now demonstrated that the synthetic biomaterial compound can be incorporated with a biodegradable polymer in such a manner to provide a variety of implants that possess sufficient mechanical strength to be used as a bone substitute in both load-bearing and non-load bearing applications and further overcomes the disadvantages associated with implants of the prior art.

SUMMARY OF THE INVENTION

The present invention provides a porous bone substitute and method of making thereof, that overcomes several of disadvantages of the prior art and meets many of the specifications outlined below.
1. Be fabricated from a material that does not invoke an adverse immunological response.
2. Promote the rapid in-growth of new bony tissue.
3. Participate in the body's natural bone remodeling process and be replaced by healthy tissue.
4. Possess an open, interconnected porous structure with the appropriate pore size, pore size distribution, porosity, and pore connectivity.
5. Be relatively inexpensive to produce and readily available.
6. Have the ability to deliver pharmaceutical agents, such as bone growth factors, in a controllable manner.
7. Be able to be readily handled and shaped by the surgeon using standard techniques.
8. Be able to be secured into place using standard orthopaedic fixation techniques without generating particulate debris that may migrate to articulating surfaces.
9. Be manufactured by a flexible process that permits gradient porosity and/or a solid shell surrounding a portion of the porous network, for example.

In accordance with the present invention there is provided a porous bone substitute that can limit fragmentation, and the subsequent migration of particulate debris, during standard orthopaedic fixation practice. The porous bone substitute is a porous ceramic composite.

In accordance with the present invention, is a composite bone substitute comprising a porous osteoinductive ceramic matrix and a biodegradable polymer. In a preferred embodiment, the biodegradable polymer is provided as a coating on the ceramic matrix. The osteoinductive porous ceramic matrix possesses optimum pore size, pore size distribution, porosity, and pore connectivity to promote the rapid in-growth of bony tissue.

In aspects of the invention, the porous matrix has a porosity of about 200 to about 600 microns.

According to an aspect of the present invention there is provided a porous ceramic composite implant, said implant comprising;
  a porous ceramic matrix having a biodegradable polymer provided on internal and external surfaces of said ceramic matrix, wherein said biodegradable polymer allows for the passage and/or delivery of a variety of agents throughout said porous ceramic matrix and improves mechanical properties of said implant.

According to another aspect of the present invention is a porous ceramic composite comprising;
  an isolated bioresorbable biomaterial compound comprising calcium, oxygen and phosphorous, wherein a portion of at least one of said elements is substituted with an element having an ionic radius of approximately 0.1 to 0.6 A and a biodegradable polymer.

According to a further aspect of the present invention is a porous ceramic composite comprising;
  a biomaterial compound having the formula:

wherein B, C and D are selected from those elements having an ionic radius of approximately 0.1 to 0.4 Å;
  x is greater than or equal to zero but less than 1;
  y is greater than or equal to zero but less than 1;
  z is greater than or equal to zero but less than 1;
  x+y+z is greater than zero but less than 1;
  j is greater than or equal to 2 but less than or equal to 4;

j is equal 4−δ, where δ is greater than or equal to zero but less than or equal to 1; and
  a biodegradable polymer.

According to a further aspect of the present invention, the biodegradable polymer coating is porous in order that the underlying osteoinductive ceramic matrix is exposed to the physiological environment and positively influence bone cell behaviour.

According to another aspect of the present invention, the polymer has a substantially high degree of porosity. In aspects the porosity is about 50 to about 200 microns.

According to a further aspect of the present invention, the biodegradable polymer itself is a composite material containing small quantities of the osteoinductive ceramic material such that cells in contact with the implant surface will be stimulated to initiate the bone repair process.

According to a further aspect of the present invention, the pores of the osteoinductive ceramic matrix are filled with a porous network of a biodegradable polymer of a composition the same as, or different, than the polymer coating.

According to a further aspect of the present invention, the porous network may be formed with a variety of polymers including photosensitive polymers. The photosensitive polymer is present during in vivo or in cell seeding, proliferation and differentiation phases of tissue formation. The photosensitive polymer is subsequently photosolubilized as the precursor to growth factor and/or cell induced vascularization of the implant.

According to a further aspect of the present invention, the hollow ligaments (struts) of the porous ceramic matrix are filled with a biodegradable polymer of a composition the same as, or different, than the polymer coating.

According to a further aspect of the present invention, the osteoinductive porous ceramic matrix is partially surrounded by a solid layer of a composition the same as, or different, than the ceramic matrix.

According to a further aspect of the present invention, the ceramic matrix possesses a gradient density with the outermost regions of the structure being the most dense and porosity increasing towards the center of the structure.

According to a further aspect of the present invention, the biodegradable polymer coating acts as a carrier and permits controlled release of selected pharmaceutical agents such as, but not limited to, bone growth factors.

According to a further aspect of the present invention, the biodegradable polymer coating acts as a carrier for living cells or genes for use in cell and/or gene therapy applications. As the biodegradable polymeric-coating degrades, cells or genes bound to or entrapped within the coating are released to the intended site of delivery.

According to a further aspect of the present invention, the osteoconductive porous ceramic matrix possesses more advantageous mechanical properties to those of the prior art as a result of repeatedly coating the organic substrate with slurries varying in solids loading.

According to a further aspect of the present invention pore size, pore size distribution, porosity, and pore connectivity of the organic foam substrate is replicated in the sintered porous body by using a vacuum or controlled gas jet to remove any excess slurry trapped within the foam structure.

According to a further aspect of the present invention, the slurry used to impregnate the organic foam substrate is sufficiently milled to produce a slurry with thixotropic rheological properties.

According to yet a further aspect of the present invention is a method of making a porous ceramic implant for connective tissue replacement, said method comprising;

(i) impregnating an organic reticulated foam structure with a slurry of calcium-phosphate compound;

(ii) drying the impregnated foam structure to form a slurry coated foam structure; and (iii) pyrolyzing the slurry coated foam structure formed in (ii) and sintering to provide a fused ceramic porous implant having a plurality of interconnected voids.

In alternative aspects, binders, wetting agents and antifoaming agents are provided to the slurry prior to impregnation of the reticulated foam structure. Furthermore, in other aspects, the organic reticulated foam structures exhibit a gradient porosity.

In any of these aspects, the porous ceramic implant may be coated with a suitable biodegradable polymer such as but not limited to polycaprolactone (PCL). In further aspects of the invention, the biodegradable polymer may be manufactured as a composite containing particles of the porous ceramic.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DETAILED DESCRIPTION OF THE PREFERRED EMBODIMENTS

The invention is directed to the manufacture and use of a porous ceramic composite comprising a sintered porous matrix body of a calcium phosphate-based compound and a biodegradable polymer. It is now surprisingly and advantageously demonstrated that the calcium-phosphate based compound described in applicant's U.S. Pat. No. 6,323,146 (the contents of which are herein incorporated by reference) can be used in conjunction with a biodegradable polymer to form a porous ceramic composite implant for both non-load bearing and load bearing in vitro and in vivo applications.

The porous ceramic composite implant of the present invention may be used generally for connective tissue replacement. The polymer allows for the passage and/or delivery of a variety of agents throughout the porous ceramic matrix which helps to provide optimum tissue in-growth. Furthermore, the biodegradable polymer coating helps to improve functional (mechanical) properties of the implant in vivo. Preferably, the porous ceramic matrix is formed from the Applicant's calcium-phosphate compound described in U.S. Pat. No. 6,323,146 (the disclosure of which is herein incorporated by reference in its entirety). In various aspects, the biodegradable polymer is provided as a continuous or discontinuous coating on the inner and outer surfaces (i.e. throughout) of the porous ceramic matrix. In another aspect, the polymer coating may also be porous and provided as a continuous or discontinuous coating throughout the porous ceramic matrix. In a further aspect, the polymer coating may have ceramic particles incorporated therein to form a polymer composite material. The ceramic particles are preferably sintered particles of the Applicant's calcium-phosphate compound described in U.S. Pat. No. 6,323,146. Alternatively, the ceramic particles may be made from a variety of calcium phosphate materials selected from the group consisting of hydroxyapatite, carbonated apatite, fluroapatite, a tricalcium phosphate, β, tricalcium phosphate, tetracalcium phosphate, octacalcium phosphate and mixtures thereof. It is also within the scope of the present invention to provide a coating (continuous or discontinuous) of biodegradable polymer that is both porous and contains ceramic particles.

In one embodiment of the invention, a porous ceramix matrix body is formed from an organic reticulated foam structure having a plurality of interconnected voids. These structures are commercially available or can be prepared, if desired. The foam structure is impregnated with an aqueous slurry such that the ligaments (struts) of the foam are coated and the voids are substantially filled. The excess slurry is removed from the pores and the coated structure is dried forming what is typically called a green body (i.e. unsintered coated foam structure). Drying make take from a few minutes to over an hour as is understood by those of skill in the art. This process is repeated until the coating of slurry attains the desired thickness throughout the foam structure. Typical thickness of coating may be about 10 to about 100 microns. The coated structure is then heated to first burn out the flexible organic foam and then sintered, thereby providing a fused ceramic foam having a plurality of interconnected voids. Heating is typically done at temperatures of about 25° C. up to about 200° C. Sintering is typically conduced at temperatures of about 900° C. to about 1300° C. The heating and sintering is done in succession such that the temperature is ramped up to the sintering temperatures.

It is desirable that the aqueous slurry used to form the porous ceramic matrix be composed of an osteoconductive or osteoinductive material that is biocompatible and actively participates in the body's natural bone remodeling process. In a preferred embodiment, the biocompatible material is Skelite™, an isolated bioresorbable biomaterial compound comprising calcium, oxygen and phosphorous, wherein a portion of at least one of said elements is substituted with an element having an ionic radius of approximately 0.1 to 0.6 Å. Specifically, this biomaterial compound has the formula:

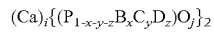

$$(Ca)_i\{(P_{1-x-y-z}B_xC_yD_z)O_j\}_2$$

wherein B, C and D are selected from those elements having an ionic radius of approximately 0.1 to 0.4 Å;

x is greater than or equal to zero but less than 1;

y is greater than or equal to zero but less than 1;

z is greater than or equal to zero but less than 1;

x+y+z is greater than zero but less than 1;

i is greater than or equal to 2 but less than or equal to 4; and j is equal 4−δ, where δ is greater than or equal to zero but less than or equal to 1.

Preparation of the slurry involves combining the ceramic material with a fluid medium, typically water, and a dispersing agent. Dispersing agents may be used to prevent agglomeration of the ceramic particles and can be either organic or inorganic. Examples of organic dispersants include sodium polyacrylate, ammonium polyacrylate, sodium citrate, sodium tartrate and mixtures thereof. Examples of inorganic dispersants include, sodium carbonate, sodium silicate, tetrasodium pyrophosphate and mixtures thereof. The quantity of dispersing agent added is typically but not limited to between about 1 and 3.5 Vol %.

It has been found that the initial particle size of the ceramic material plays a role in the strength of the final product. In addition, particle size significantly influences both the solid loading capability and the resulting viscosity of the slurry. Milling a portion of the slurry has been found to be useful in obtaining the desired particle size distribution. Typically, a portion of the slurry is milled between 1 and 24 hrs using an inert, abrasive-resistant milling media such as alumina or zirconia to provide ceramic particles of about up to 50 microns (and any size or ranges in size up to about 50 microns). In order for the ceramic particles of the slurry to adhere to both the foam substrate and to each other, it is desirable that, after particle size reduction, the slurry is thixotropic in nature. That is, viscosity of the slurry is reduced under increasing rates of shear.

Prior to impregnating the reticulated foam body, additives may also be added to the slurry. These may include a binder, to impart strength to the green body, a wetting agent, to improve distribution of the slurry throughout the foam, and an antifoaming agent that reduces the formation of bubbles in the slurry. These components are added to the slurry in small amounts, typically but not limited to less than about 10 vol % for the binder and less than about 2 vol % for the wetting and antifoaming agents.

It has been found that good compressive strength, about 10 MPa, can be achieved by applying several coats and drying the impregnated structure between each coating. While the porous structure of the foam may begin to become clogged as the latter coats are applied, it has been found that using a slurry with a high solids loading (up to about 30 Vol %) for the first several coats, followed by several coats with a slurry possessing a lower solids loading (below about 20 Vol %) helps to avoid any clogging.

In the present invention, an effective method of removing the excess slurry is to use a vacuum process. In this case, the impregnated foam is placed onto a mesh screen fitted to the top of a vertically mounted vacuum hose and the excess slurry is drawn through the hose into the vacuum unit. Alternately, a controlled gas jet can be used to disperse excess slurry that occludes internal pores.

To remove the organic reticulated foam structure, the dried coated structure is transferred to an electric furnace and heated to and held at a temperature sufficiently high (i.e. up to about 200° C.) to pyrolyze the underlying polymer foam. Subsequent sintering of the ceramic structure (at temperatures of up to about 1300° C., more preferably about 1000° C. to about 1300° C.) is performed by heating to a temperature significantly higher than the temperature used to pyrolyze the foam. The furnace is then allowed to cool to room temperature.

A porous structure exhibiting gradient porosity can be manufactured by using centripetal force to distribute the slurry to the outer surface of the reticulated structure. This can be accomplished by rotating a cylindrical reticulated foam body inside a tube whose interior is lined with an absorbent material. A hollow channel down the center of the reticulated foam body permits a nozzle to travel along the long axis of the reticulated cylindrical part. Slurry is fed through the nozzle as the tube is rotated. Beginning at the far end of the reticulated part, the nozzle travels the length of the tube, via a linear drive, coating the spinning reticulated foam structure. The absorbent material secured to the inner surface of the tube dewaters the adjoining slurry and so permits the accumulation of slurry at the outer surface of the reticulated cylinder. A porous ceramic body exhibiting gradient porosity is produced by repeating this process while altering important processing variables such as tube rotational speed, slurry spray pressure, nozzle travel speed, and slurry solids loading.

In an alternative embodiment for producing a porous implant with gradient porosity, the foam is modified so that it possesses a gradient porosity prior to replication. This can be accomplished by coating the foam in an appropriate thermally decomposable material, such as wax, and centrifuging the wax-coated foam to force the molten wax to the outer surfaces of the foam. Gradient porosity can be accomplished by repeating this process several times. Once the desired gradient porosity is attained, the foam structure can be replicated using the standard replication technique previously described.

In yet another further embodiment of producing a porous implant with gradient porosity, the polymer foam is preformed by physical distortion combined with the application of heat or physical restraint to retain the distorted shape throughout the ceramic replication process. The distorted shape can be configured to provide a continuous gradient or selected steps in pore size and pore geometry.

In a further embodiment of the present invention, and prior to the provision of any biodegrable polymer, a solid outer layer partially surrounding the porous ceramic body may be formed by filling the interstices of the sintered porous body with a thermally or chemically decomposable material, such as wax or calcium sulfate, and using a slip casting process to coat selected surfaces with a solid ceramic coating. If a thermally decomposable material such as wax is used to fill the interstices of the porous body, thermal processing will serve to melt and pyrolyze the wax followed by sintering of the dense exterior shell. This provides an implant that is similar to cortical or long bone.

The present invention provides a porous bone substitute (i.e. porous ceramic matrix) that minimizes fragmentation, and the subsequent migration of particulate debris, during standard orthopedic fixation practice. The porous ceramic matrix can be made of various sizes, shapes, porosity, degree and sizes of porosity and including different gradient porosities. This is particularly important for implant applications occurring in close proximity to articular surfaces and is further accomplished by applying a biodegradable polymeric coating to the surfaces of the porous ceramic matrix.

In order to form a porous ceramic compositie the porous ceramic matrix is further provided with a biodegradable polymer. A method of applying a biodegradable coating to the above described porous ceramic matrix (body or structure) first involves selecting a polymer that possesses the appropriate mechanical and degradation properties. Suitable polymers are known to those of skill in the art. Once such a polymer has been selected, it is dissolved in an appropriate solvent. The porous ceramic matrix is placed into a mold and the polymer/solvent solution (typically about 5-15% by weight polymer in solvent solution) is allowed to infiltrate the interstices and encapsulate the outer surfaces of the porous ceramic body. The mold is placed under reduced pressure and the solvent is allowed to evaporate until a polymer coating of a desired thickness (about up to 250 microns and any range or ranges thereof) is applied to both the external and internal surfaces of the porous ceramic matrix. It is understood to those of skill in the art that the biodegradable polymer coating can be provided on the porous ceramic matrix as a continuous or discontinuous coating.

As is understood by one of skill in the art, a variety of biodegradable polymers may be used in the practice of the invention. Such polymers include but are not limited to photosensitive polymers; polyhydroxybutyrate (PHB) and polyhydroxyvalerate (PHV) and copolymers thereof; polycaprolactone (PCL); polyanhydrides; poly (ortho esters); poly (amino acids) and psuedo-poly (amino acids); polyethylene glycol (PEG); and, polyesters such as poly(lactic acid) (PLA) and poly(glycolic acid) (PGA) and copolymers thereof. It is also understood by one skilled in the art that the different types of polymers and copolymers may be combined for use.

The above described method is advantageous due to the fact that polymer coatings can be applied at ambient temperatures, thus permitting the incorporation of pharmaceutical agents, such as but not limited to bone growth factors, into the polymer coating. Through proper selection of the polymeric material, an appropriate dose release profile may be achieved. Suitable pharmaceutical agents may include but are not limited to antimicrobials, antibiotics (i.e. Tobramycin), epidermal growth factor, fibroblast growth factor, platelet derived growth factor, transforming growth factor, parathyroid hormone, leukemia inhibitory factor, insulin-like growth factor, bone morphogenetic protein, osteogenin, sodium fluoride, estrogens, calcitonin, biphosphonates, calcium carbonate, prostaglandins, vitamin K and mixtures thereof.

In a further embodiment of the present invention, the biodegradable polymer coating of the present invention may be made to be porous through the use of an appropriate pore forming agent. In still a further embodiment, the biodegradable coating, whether porous or not, may be made to be a composite coating by adding discrete particles of a ceramic phase. In this aspect, ceramic particles are added into the polymer/solvent solution prior to coating.

As the thickness of the polymeric coating may be varied and controlled, a preferred embodiment is the formation of a continuous porous biodegradable polymeric phase throughout the interstices of the porous ceramic matrix and is readily fabricated through the use of pore forming agents and extended immersion times.

One advantage of the present invention involving the replication technique is that the ligaments (struts that compose the web of the ceramic body) of the final structure are hollow. This provides a means to improve the toughness of the porous ceramic body by filling these channels with an appropriate polymer. This can readily be achieved by infusing the entire ceramic body with a polymer solution, including the hollow ligaments. This process is aided by the infusion of the polymer while the ceramic body is under vacuum, as the presence of the vacuum eliminates the potential for entrapped air within the hollow ligaments. Once the entire structure contains the desired polymer within the open voids is removed via vacuum or controlled gas jet. This then leaves the hollow ligaments filled with the polymer to impart increased toughness and limiting the potential for fragmentation at the time of surgical implantation.

In summary, the present invention provides a porous bone substitute ("implant") that has numerous advantages and uses in the field of orthopedics and dentistry both in vitro and in vivo. As an implant, the porous bone substitute can be used in both non-load bearing and load-bearing applications. The present invention also has use in cell therapy applications for the repair and/or regeneration of patient tissue by introducing the appropriate living cells within the micropores of the porous implant. Some candidate cells may include for example, cartilage cells, tendon cells, bone cells, ligament cells, organ cells, musculotendinous cells and mixtures thereof. Teeth or portions thereof may also be incorporated within the porous ceramic matrix. The present invention also has use in gene therapy applications where the porous bone substitute can be used as a delivery device for genetically altered cells to produce a desired biological agent at a desired site.

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of chemistry and general processing methods for the ceramics referred to but not explicitly described in this disclosure and examples are reported in the scientific literature and are well known to those skilled in the art.

Example 1

Preparation of Polymer-Coated Porous Ceramic Body

An open pore polyurethane foam with dimensions 12 mm×24 mm×60 mm was provided. Two aqueous ceramic slurries were provided. One slurry had a 25 vol % solids loading and the other a 17 vol % solids loading. Both slurries had been ball milled for 5 hrs and were thixotropic in nature. The foam material was immersed into the 25 vol % solids slurry and agitated to remove air, to substantially fill the voids with the slurry, and to coat the ligaments (struts) of the foam with the slurry. The resultant impregnated foam was removed from the slurry and placed onto a mesh screen that was attached to a vertically mounted vacuum hose. Excess slurry was removed from the voids by turning on the vacuum unit for 3-5 seconds. This was sufficient time to remove excess slurry from the voids of the foam without disrupting the slurry that was adhered to the struts of the foam. The coated foam was oven dried at 90° C. for 15 minutes. This entire process was repeated 1-2 more times with the 25 vol % solids slurry and 4-5 more times with the 17 vol % solids slurry.

The dried coated foam substrate was transferred to an electric furnace where it was heated at a rate of 1° C./min to a temperature of 500° C. to drive off water and to allow the polyurethane foam to pyrolyze without collapsing the ceramic scaffold. The foam was held at 500° C. for 4 hrs and was, subsequently, heated, at a rate of 1° C./min, to a temperature of 1175° C. This temperature was held for 1 hr to permit the ceramic particles to sinter together thereby providing an open cell ceramic foam possessing the physical morphology of the original polyurethane foam material. Subsequently, the furnace was cooled at a rate of 36° C./min until a final temperature of 25° C. was achieved. The final dimensions of the sintered ceramic foam were 10 mm×20 mm×50 mm.

A polymer solution was provided by dissolving 5 g of polycaprolactone (PCL) in 95 g of dichloromethane. The solution was stirred in a beaker for approximately 15 hrs at 225 rpm to ensure that the PCL was completely dissolved. The sintered porous ceramic was then placed in a Teflon mold and infiltrated with the polymer solution. The mold containing the polymer impregnated sintered body was, subsequently transferred to a vacuum desiccator for 20 minutes. This process was repeated 4 more times using decreasing volumes/concentrations of PCL solution each time. The polymer-coated scaffold was then dried for 15-20 hrs in the desiccator resulting in a polymer reinforced ceramic body exhibiting improved fracture toughness.

Example 2

Preparation of Polymer-Coated Porous Ceramic Body with Ceramic Particles

A polymer-coated porous ceramic body was produced as in example 1. In this case, ceramic particles of a composition the same as the sintered porous body were included into the PCL/dichloromethane solution. These ceramic particles had a mean particle size of 6 µm and had been calcined at a temperature of 1000° C. for 1 hr. The polymer/dichloromethane solution had a ceramics solid loading between 20-30 vol %. Application of the polymer/ceramic composite coating to the sintered porous ceramic was carried out as in example 1. This resulted in the production of a thin composite coating consisting of discrete particles of the ceramic material distributed evenly throughout the polymer matrix.

Example 3

Preparation of Polymer-Coated Porous Ceramic Body with Pore Forming Agents

A polymer-coated porous ceramic body was produced as in example 1. In this case, pore forming agents were included in the polymer/dichloromethane solution. Examples of pore forming agents suitable for this application include polymer or wax beads with melting and vaporization temperatures lower than that of PCL. The pore forming agent was included into the PCL/dichloromethane solution at levels between 30-40 vol %. The polymer coating was applied to the porous ceramic body as described in example 1. The coated porous ceramic body was subsequently transferred to an oven and heated to a temperature greater than the melting point of the chosen pore forming agent but below the melting temperature of the PCL coating (64° C.). This thermal treatment caused the pore forming agent to volatize and produced a thin porous polymer coating on both the internal and external surfaces of the porous ceramic body.

Example 4

Method for Production of a Porous Ceramic Body Exhibiting Gradient Porosity An open pore polyurethane foam cylinder measuring 50 mm in diameter and 13 mm in length was provided. A hole measuring 25 mm OD was produced through the center of the foam cylinder using a 25 mm ID punch. The resulting foam tube was placed inside an aluminum cylindrical shell measuring 55 mm ID and 150 mm in length that had been lined with an absorbent material.

Two aqueous ceramic slurries were provided. One slurry had a 25 vol % solids loading and the other a 17 vol % solids loading. Both slurries had been ball milled for 5 hrs and were thixotropic in nature. Using a peristaltic pump, the 25 vol % solids slurry was pumped through a nozzle that could be translated along the central axis of the aluminum cylindrical shell via a support mounted on an external linear drive. The aluminum shell containing the polyurethane foam ring was rotated at a speed of 375-700 rpm while the nozzle, dispensing a fine mist of slurry, traveled along the axis of the rotating assembly. This process was repeated 1-2 more times with the 25 vol % slurry and 4-5 more times with the 17 vol % solids slurry such that the foam ring was substantially coated and a density gradient was established with the outer surfaces of the foam substrate being the most dense and porosity increasing towards the center of the part. The coated foam ring was subsequently transferred to an electric furnace and processed as described in example 1 to produce a porous ceramic body exhibiting gradient porosity.

Example 5

Production of a Porous Ceramic Body Exhibiting Gradient Porosity

A open pore polymeric foam precursor exhibiting gradient porosity was manufactured using rapid prototyping techniques such as sterolithography, fused deposition modeling, and 3D printing. The polymeric component was subsequently processed into a porous ceramic body exhibiting gradient porosity using the replication technique as discussed above.

Example 6

Production of a Porous Ceramic Body Exhibiting a Solid Exterior Shell

A porous ceramic body with a solid exterior shell was produced by repeatedly immersing an open pore polyurethane foam precursor into a thixotropic slurry, removing the excess slurry with a vacuum, and sintering the green body at temperatures in excess of 1000° C. for a period greater than about 1 hr. The sintered porous ceramic body was subsequently infiltrated with molten wax such that, after cooling, all of the pores of the sintered ceramic body were plugged with solid wax. The infiltrated piece was subsequently shaped into the desired final shape and placed in a slip casting mold that was slightly larger than the infiltrated ceramic body. The mold was subsequently filled with a ceramic slip and allowed to dry. The new green body was carefully removed from the mold and sintered at a temperature in excess of about 1000° C. for a period of about 1 hr or more. This high temperature processing served to sinter and densify the solid exterior shell and pyrolyze the wax such that the pores of the sintered body were re-opened.

Example 7

Production of a Porous Ceramic Body Exhibiting a Solid Exterior Shell

A porous ceramic body with a solid exterior shell was produced by inserting a cylindrical open pore polyurethane foam precursor into a sleeve of a pyrolyzable material, such as polystyrene, and immersing the entire structure into a thixotropic slurry. Excess slurry was subsequently removed by using a vacuum and the ceramic coating given sufficient time to dry. This process was repeated until the ceramic coating attained the desired thickness at which point the entire structure was sintered at a temperature in excess of about 1000° C. for a period greater than about 1 hr. This high temperature processing served to sinter the ceramic body together and pyrolyze both the open pore polyurethane foam and the polystyrene sleeve. The end result was a porous ceramic body with an exterior solid shell.

Example 8

Method for the Production of an Open Pore Ceramic Body

The excess slurry deposited during the replication technique was removed in order that the pores of an open pore polyurethane foam precursor remained open throughout the replication process during application of multiple coatings of a ceramic material. The method involved removing the excess slurry by placing the slurry infiltrated foam precursor onto a mesh screen that was either attached to a vertically mounted vacuum hose or placed across an opening in a vacuum box, and removing the slurry by turning the vacuum on for several seconds. This process could be enhanced by using a jet or curtain of compressed air in combination with the vacuum to push the excess slurry through the foam and into the vacuum hose or box. Proper design of the vacuum system enabled a large fraction of the expelled slurry to be reclaimed and reused during subsequent coatings.

Example 9

Method for the Production of an Open Pore Ceramic Body

An open pore ceramic body was produced using rapid prototyping (RP) techniques. In this method, an osteoconductive/osteoinductive ceramic powder was obtained and formed into a sintered porous ceramic body using rapid prototyping techniques such as selective laser sintering (SLS). An alternative method for producing a sintered porous ceramic body using RP techniques was to first coat the ceramic particles with an appropriate polymer/binder then use low temperature SLS to effectively bind the ceramic particles together. Subsequent high temperature thermal processing served to pyrolyze the polymer/binder while sintering together the ceramic particles. An additional technique used to form the porous green body was to apply a binder to a bed of ceramic powder using ink jet printer technology. The green body was subsequently processed at high temperatures to pyrolyze the binder and sinter the ceramic particles together. In all aspects of this example, the porous ceramic body was manufactured by the successive build up of layers as is typical of all rapid prototyping technologies. As the part is created from a CAD model, the formation of components exhibiting gradient porosities, dense cortical shells and varying geometries is readily achievable.

Although preferred embodiments of the present invention are described in detail herein, it will be understood by those skilled in the art that variations may be made thereto without departing from the spirit of the invention.

We claim:

1. An implant comprising:
a sintered matrix body of a calcium phosphate-based compound, the sintered matrix body possessing an open interconnected porous structure with internal and external surfaces; and
a biodegradable polymer coating provided throughout the sintered matrix body on the external and internal surfaces of the open interconnected porous structure, wherein the biodegradable polymer coating still allows for the passage and/or delivery of agents and/or cells throughout the open interconnected porous structure and improves the mechanical properties of the sintered matrix body, the biodegradable polymer coating forming a discontinuous coating throughout the internal and external surfaces of the open interconnected porous structure;
wherein the biodegradable polymer coating includes a polymer selected from the group consisting of photosensitive polymers, polycaprolactone, polyanhydrides, poly(ortho esters), poly(amino acids), pseudo-poly(amino acids), polyethylene glycol, polyesters and mixtures thereof.

2. The implant of claim 1, wherein the interconnected porous structure has pores of about 200 microns to about 600 microns 3. The implant of claim 1, wherein the biodegradable polymer coating has pores of about 50 to about 200 microns.

4. The implant of claim 1, wherein the biodegradable polymer coating is a composite material comprising a biodegradable polymer and ceramic particles.

5. The implant of claim 4, wherein the ceramic particles have the same composition as the sintered matrix body.

6. The implant of claim 4, wherein the ceramic particles have a particle size of not greater than about 50 microns.

7. The implant of claim 1, wherein the photosensitive polymers are selected from the group consisting of polyhydroxybutyrate, polyhydroxyvalerate and copolymers thereof.

8. The implant of claim 1, wherein the polyester is selected from poly(lactic acid) and poly(glycolic acid).

9. The implant of claim 1, wherein the biodegradable polymer coating includes polycaprolactone.

10. The implant of claim 1, wherein the biodegradable polymer coating has a thickness not greater than about 250 microns.

11. The implant of claim 1, wherein the biodegradable polymer coating includes a pharmaceutical agent incorporated therein.

12. The implant of claim 11, wherein the pharmaceutical agent is an agent selected from the group consisting of epidermal growth factor, fibroblast growth factor, platelet derived growth factor, transforming growth factor, antimicrobials, antibiotics, parathyroid hormone, leukemia inhibitory factor, insulin-like growth factor, bone morphogenetic proteins, osteogenin, sodium fluoride, estrogens, calcitonin, biphosphonates, calcium carbonate, prostaglandins, vitamin K and mixtures thereof.

13. The implant of claim 1, wherein the sintered matrix body is loaded with a population of cells selected from the group consisting of cartilage cells, tendon cells, bone cells, ligament cells, organ cells, musculotendinous cells and mixtures thereof.

14. The implant of claim 1, wherein the calcium phosphate-based compound is a compound comprising calcium, oxygen and phosphorous, wherein a portion of at least one of said elements is substituted with an element having an ionic radius of approximately 0.1 to 0.6 Å.

15. The implant of claim 14, wherein the compound has the formula:

$$(Ca)_i\{(P_{1-x-y-z}B_xC_yD_z)O_j\}_2$$

wherein B, C and D are selected from those elements having an ionic radius of approximately 0.1 to 0.4 Å;
x is greater than or equal to zero but less than 1;
y is greater than or equal to zero but less than 1;
z is greater than or equal to zero but less than 1;
x+y+z is greater than zero but less than 1;
i is greater than or equal to 2 but less than or equal to 4; and
j is equal 4−δ, where δ is greater than or equal to zero but less than or equal to 1.

16. The implant of claim 1, wherein the sintered matrix body has a gradient density.

17. The implant of claim 16, wherein an outermost region of the sintered matrix body is partially surrounded by a solid layer of a composition the same as the ceramic phosphate-based compound.

18. The implant of claim 1, wherein sintered matrix body has hollow ligaments.

19. The implant of claim 18, wherein the hollow ligaments are filled with the biodegradable polymer.

20. An implant comprising:
   a sintered matrix body possessing an open interconnected porous structure with internal and external surfaces, the open interconnected porous structure including pores of about 200 microns to about 600 microns, the sintered matrix body comprising calcium, oxygen and phosphorous, wherein a portion of at least one of said elements is substituted with an element having an ionic radius of approximately 0.1 to 0.6 Å; and
   a biodegradable polymer coating provided throughout the sintered matrix body on the external and internal surfaces of the open interconnected porous structure, wherein the biodegradable polymer coating still allows for the passage and/or delivery of agents and/or cells throughout the open interconnected porous structure and improves the mechanical properties of the sintered matrix body, the biodegradable polymer coating forming a discontinuous coating throughout the internal and external surfaces of the open interconnected porous structure and having pores of about 50 to about 200 microns;
   wherein the biodegradable polymer coating includes a polymer selected from the group consisting of photosensitive polymers, polycaprolactone, polyanhydrides, poly(ortho esters), poly(amino acids), pseudo-poly (amino acids), polyethylene glycol, polyesters and mixtures thereof.

21. The implant of claim 20, wherein the biodegradable polymer coating includes a biodegradable polymer and ceramic particles.

* * * * *

UNITED STATES PATENT AND TRADEMARK OFFICE
CERTIFICATE OF CORRECTION

| | | |
|---|---|---|
| PATENT NO. | : 7,875,342 B2 | Page 1 of 1 |
| APPLICATION NO. | : 10/490492 | |
| DATED | : January 25, 2011 | |
| INVENTOR(S) | : Smith et al. | |

It is certified that error appears in the above-identified patent and that said Letters Patent is hereby corrected as shown below:

IN THE SPECIFICATIONS:

In Column 2, Line 8, delete "WO99119003." and insert -- WO99/19003. --, therefor.

In Column 5, Line 62, delete "0.6A" and insert -- 0.6Å; --, therefor.

In Column 8, Line 5, delete "a" and insert -- α --, therefor.

In Column 8, Line 6, delete "β," and insert -- β --, therefor.

In Column 8, Line 28, after "25°C." delete "up".

IN THE CLAIMS:

In Column 16, Line 6, in Claim 2, delete "microns" and insert -- microns. --, therefor.

Signed and Sealed this
Twelfth Day of April, 2011

David J. Kappos
*Director of the United States Patent and Trademark Office*